United States Patent [19]

Nakatani et al.

[11] Patent Number: 4,683,249
[45] Date of Patent: Jul. 28, 1987

[54] AMIDINES AND A METHOD OF MANUFACTURING THE SAME

[75] Inventors: Keiichi Nakatani, Kyoto; Shohzo Ohnishi, Sakura; Tadamasa Kurosaki, Ohtsu, all of Japan

[73] Assignee: San-Apro Kabushiki Kaisha, Kyoto, Japan

[21] Appl. No.: 850,448

[22] Filed: Apr. 8, 1986

[30] Foreign Application Priority Data

Apr. 9, 1985 [JP] Japan .................................. 60-76209
Jul. 15, 1985 [JP] Japan ................................. 60-156341

[51] Int. Cl.$^4$ ............................................. C08G 18/14
[52] U.S. Cl. ...................................... 521/129; 528/54; 528/94; 528/118; 528/408; 528/417; 540/579
[58] Field of Search .................... 521/129; 528/54, 94, 528/118, 408, 417; 540/579

[56] References Cited

U.S. PATENT DOCUMENTS 3,622,540 11/1971 Hashimoto et al. .................. 260/47
3,769,244 10/1973 Hashimoto et al. ................. 260/2.5

*Primary Examiner*—Maurice J. Welsh
*Attorney, Agent, or Firm*—Browdy and Neimark

[57] ABSTRACT

Amidines of the formula:

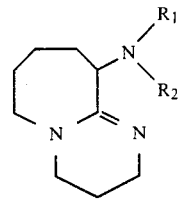

wherein $R_1$ and $R_2$ are alkyl groups and the sum of the carbons in $R_1$ and $R_2$ is from 2 to 16 are produced by cyanoethylation of the lactam:

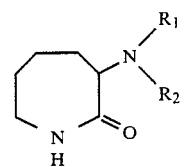

wherein $R_1$ and $R_2$ are as defined above, followed by reduction and, finally, cyclization by dehydration. The compounds produced are useful for curing epoxy and urethane resins.

8 Claims, No Drawings

AMIDINES AND A METHOD OF MANUFACTURING THE SAME

BACKGROUND OF THE INVENTION (a) Field of the Invention

This invention relates to novel amidine compounds, the manufacturing method and the use of the compounds as epoxy curing catalysts and urethane catalysts.

(b) Description of the Prior Art

The compound having an amidine structure in a molecule, 1,8-diazabicyclo(5,4,0)undecene-7(DBU, hereafter referred to simply as DBU) or the like is known to be a strong base having a pKa of 11.5, and is used as the epoxy curing catalyst, the urethane catalyst and the like. But DBU has the following defects: It is very hygroscopic and is hard to handle in rainy season and summer, and the cured products have high water absorption ratios in the case of the use of DBU as the epoxy curing catalyst.

SUMMARY OF THE INVENTION

In order to solve the above defects of the amidines, the present invention is completed by discovering that the novel amidine compound improve the above problems.

The novel amidine in the present invention is represented by the general formula(1), namely 6-disubstitutedamino-1,8-diazabicyclo(5,4,0)undecene-7.

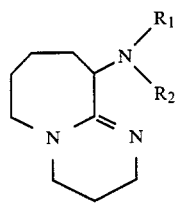

formula (1)

In formula (1), each of $R_1$ and $R_2$ in independently an alkyl group having $C_1$ to $C_{14}$ or benzyl group. The sum of carbon atoms is 2 to 16 and more preferably 3 to 16. In the case in which the sum of carbon atoms is 1, the effect of non-water solubilization is not sufficient. In the case of the carbon atom sum more than 17, it becomes to be difficult to purify by distillation and it is not preferable that too much addition amount is needed on the use of epoxy and urethane catalysts. Therefore, the most preferable sum of carbon number is 6 to 13. The alkyl group is generally straight chain, and may be branched chain.

DETAILED DESCRIPTION OF THE INVENTION

The novel amidines in the present invention are, for example, 6-dimethylamino-1,8 diazabycyclo(5,4,0)undecene-7 (referred to herein as DMA-DBU) 6-methyl-butylamino-1,8-diazabicyclo(5,4,0)undecene-7, 6-methyloctylamino-1,8-diazabicyclo(5,4,0)undecene-7 [hereafter referred to simply as MOA-DBU] 6-dibutylamino-1,8-diazabicyclo(5,4,0)undecene-7 (hereafter DBA-DBU), 6-butyl-benzylamino-1,8-diazabicyclo(5,4,0)undecene-7 (hereafter BBzA-DBU), 6-dihexyl-amino-1,8-dazabicyclo(5,4,0)undecene-7 and the like. Each of the above compound can be used by itself or in the form of a mixture.

The novel amidine compounds in the present invention can be manufactured by cyanoethylation of the lactam compound represented by the formula(2), reduction and then the cyclization by dehydration.

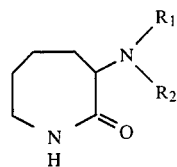

formula (2)

(In formula (2), each of $R_1$ and $R_2$ is the same meaning as in formula (1).)

The lactam compounds of formula (2) are for example manufactured by known alkylation or benzylation methods of 3-amino-2-oxohexamethyleneimine.

Generally, acrylonitrile is employed for the cyanoethylation of the above lactam. The molar ratio of acrylonitrile to the lactam compound is nearly 1, and after the completion of the reaction, unreacted raw ingredient can be recovered. The reaction conditions of the cyanoethylation are the same as in the previous ones, for example in Organic Reactions 5, 79 to 135 (1949). This reaction needs alkaline catalysts. For example, these catalysts involve KOH, NaOH, benzyltrimethyl ammonium hydroxide, Na alkoxides and the like. The used amount of the catalyst is below 5%, preferably 1 to 2%. The reaction temperature is between 50° and 100° C., preferably between 75° and 95° C. The mixture of the above lactam and the catalyst is heated to the above reaction temperatures and, under stirring, acrylonitrile is added dropwise. In advance, less than 1%, preferably 0.5 to 0.004%, of polymerization inhibitors, such as hydroquinone or hydroquinone mono-methylether, can be added into acrylonitrile in order to avoid polymerizing acrylonitrile. The cyanoethylation reaction is exothermic and the reaction temperature can be controlled by charge speed of acrylonitrile. After the addition of acrylonitrile, the reaction is completed by stirring at the same temperatures for about 3 hours. And for the reaction, aromatic solvents such as xylene, benzene, toluene and the like, and dioxane and the like, which aren't reactive with acrylonitrile, may be used as the reaction solvent. After the reaction, if necessary, the cyanoethylated product, can be isolated by vacuum distillation.

The nitrile group of the thus obtained cyanoethylated product can be reduced to the primary amino group by means of conventional hydrogenation. For example, 100 g of a cyanoethylated product are hydrogenated in the presence of about 8 g of liquid ammonia and about 4 g of Raney Nickel at 100° to 120° C. under hydrogen pressure of 50 kg/cm². The reaction is completed in about 3 hours.

Then, the cyclization by dehydration of thus obtained N(3-aminopropyl)amide compound consists of heating the compound, in the absence of the catalyst or in the presence of the acid catalyst such as phosphoric acid, p-toluene sulfonic acid, antimony trioxide, and the like, with a solvent (bp. 70° to 250° C.) such as hydrocarbons (benzene, toluene, xylene, tetralin, pseude cumene and the like), alcohols and glycols (ethanol, octanols, ethyleneglycol, propyleneglycol and the like), and the like which can form an azeotropic mixture with water, and removing the water produced by dehydration reaction out of the system. When the acid catalyst is used, the used amount is 0.1 to 5%, preferably 0.5 to 2.0, for the amount of the N(3-aminopropyl)amide compound. The amount of azeotropic solvent used for dehydration is 0 to 500% preferably 20 to 100% for the amount of the N(3-aminopropyl)amide. The end point is determined by measurement of the amount of the water removed out of the system and total amine value (HCl method) of the reaction product. In this case, the total amine value (HCl method) of unreacted 3-disubstitutedamino-1-(3'-aminopropyl)-2-oxohexamethylene imine represented by formula (3) is determined as mono-valent base, though the compound has an amidine and N,N-disubstitutedamino groups in the molecule. The objective compound can be isolated by means of vacuum distillation and the like after the removal of azeotropic solvent.

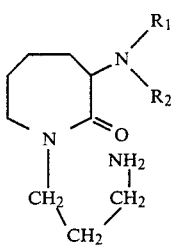

formula (3)

(In formula (3), each of $R_1$ and $R_2$ is the same meaning as in formula (1).)

The novel amidine compound in the present invention, as well as its salts or organic and inorganic acids, can be used as curing catalyst for epoxy resins. The organic and inorganic acids are, for example, straight chain fatty acids (for example, acetic acid, propionic acid, caproic acid, lauric acid and stearic acid), unsaturated fatty acids (for example, acrylic acid, crontonic acid, oleic acid, linoleic acid and linolenic acid), isoalkyl fatty acids (for example, 2-ethylhexoic acid), oxyfatty acids (for example, lactic acid, glycolic acid, ricinoleic acid and hydroxystearic acid), dibasic fatty acids (for example, succinic acid and adipic acid), aromatic acid (for example, benzoic acid, salicylic acid, phthalic acid and terephthalic acid), phenols (for example, phenol, cresol, resorcin, catechol and phenol novolac resin), organic phosphoric esters (for example, dibutyl phosphate and monolauryl phosphate), sulfuric esters, sulfation products (for example, lauryl sulfate and dodecylbenzenesulfonic acid), enol acids (for example, barbituric acid), tetraphenyl boric acid and inorganic acids (for example, carbonic acid, sulfuric acid, phosphoric acid and hydrochloric acid).

The preparation method of the salts is accomplished by stirring, mixing and melting the novel amidine and an acid by heating if necessary, and the solvent which may be used therewith. The solvent may be removed by means of distillation after the neutralization reaction.

The epoxy resins used in the present invention are mentioned in Encyclopedia of Polymer Science and Technology 6, 209 to 271 (1967) published by Interscience Publishers, etc. The epoxy resins are, for example, cyclopolyepoxy compounds such as vinylcyclohexene diepoxide, dicyclopentadiene diepoxide, ethyleneglycol bis (3.4-epoxy tetra hydrodicyclopentadiene-8-yl) ether and the like; compounds having two epoxycylohexyl groups [diethyleneglycol bis (3,4-epoxycyclohexane carboxylate), bis-3,4-(epoxycyclohexylmethyl)-succinate and the like], polyglycidyl ester compounds obtained by the reaction between dicarboxylic acids and epichlorohydrin in the presence of alkali, and polyglycidyl ether compounds obtained by etherification reaction in the presence of alkali of epichlorohydrin or dichlorohydrin with dihydric alcohols, polyhydric alcohols, diphenols (for example, bisphenol A, tetrabromobisphenol A, bisphenol F, bisphenol S, condensed products between acetaldehyde and phenol); polyphenols or novolac resins such phenol novolac resins, o-cresol novolac resins and the like. A mixture of more than two kinds of the above epoxy compounds can be used.

In the present invention, not only epoxy resins by themselves but so-called epoxy hardeners which react with epoxy compounds can be co-used. These examples are mentioned in the above Encyclopedia of Polymer Science and Technology 6, 209 to 271 (1967), J. of The Adhesion Society of Japan 15, 102 and 141 (1979), and Polymer Application (in Japanese) 25, 383 (1976), and 26, 64, 120 and 184 (1977). Epoxy hardeners are aliphatic amines such as diethylenetriamine, triethylene tetramine, diethylaminopropylamine and the like; cyclic aliphatic polyamines such as N-amino-ethylpiperazine, isophorone diamine and the like; amines having an aromatic ring, such as xylene diamine and its polymers, phenylene diamine and diaminodiphenyl-methane and -sulfone; polyamides such as Polymide L-type, manufactured by Sanyo Chemical Industries, Ltd.; modified amines (for example, ethylene oxide- propylene oxide- and epoxy resin-modified amines; cyanoethylated amines; ketiminized amines, phenol/formaldehyde-modified amines); polymercaptans such as Dion 3-800LC and Thiokol LP; acid anhydrides such as phtahalic anhydride, maleic anhydride, trimellitic acid anhydride, pyromellitic acid dianhydride, benzophenone tetracarboxylic dianhydride, methyl nadic anhydride, tetra- or hexahydro phthalic anhydride, methyl hexahydro phthalic anhydride and halogenated products of the above acid anhydrides; mono- and polycarboxylic acids, substituted and non-substituted, such as 2-ethylhexoic acid, benzoic acid, salicylic acid, adipic acid, phthalic acid, dodecane dicarboxylic acid, hydroxy stearic acid, trimellitic acid and the like; amino resins such as butylated melamine resins and butylated urea resins; primary condensation products of synthetic resins such as formaldehyde condensation products with p-oxybenzoic acid, phenol resins and poly (p-vinylphenol) resin; mono- and polyhydric phenols such as phenol, resorcin and the like; alcohols and glycols such as decylalcohol, stearyl alcohol, ethylene glycol, trimethylolpropane and the like; isocyanates such as tolylene diisocyanate, crude diphenylmethane diisocyanate, hexamethylene diisocyanate, isophorone diisocyanate and the like; reaction products of the above isocyanates with active hydrogen compounds such as glycols, water and the like, polymerized products of the above isocyanates; dicyandiamide and hydrazine derivatives such as organic acid hydrazide.

Especially, the novel amidine compound in the present invention wherein $R_1$ and $R_2$ are both methyl groups, and its salts of organic and inorganic acids, are adequate for the curing reaction of o-cresol novolac epoxy resins (obtained by the reaction between o-cresol novolac resin and epichlorohydrin) with phenol novolac resins, and the above compound is used for the packaging of semiconductors.

The used amount of the novel amidines in the present invention and their salts is generally 0.01 to 20 parts by weight, preferably 0.1 to 5 parts by weight for 100 parts by weight of epoxy compound.

The novel amidines and their salts in the present invention may be used with the known catalysts such as secondary and tertiary amines such as dimethyl benzylamine, 2,4,6-tris(dimethylaminomethyl)phenol, 1,3,5-tris(dimethylaminopropyl)hexahydro-s-triazine, tetramethylguanidine, 2-methyl imidazole, 2-ethyl-4-methyl imidazole, DBU and its salts; Lewis acids such as $BF_3$ and their amine salts.

And furthermore, the novel amidine and its salts of organic and inorganic acids can be used as the reaction catalyst for isocyanate compounds. The kinds of the organic and inorganic acids used, and preparation methods for the salts of the novel amidines are the same as the above mentioned.

The reactions of isocyanate compounds in the present invention involve those with compounds having active hydrogen, as defined by the Zerewitinoff method, those of uretidinedione or isocyanate formation by means of dimerization or trimerization of isocyanates, and those of carbodiimide formation by means of decarboxylation from 2 mole isocyanates.

The polyisocyanates and the polyols as the active hydrogen compounds used in the present invention involve all of the raw ingredients generally used for the manufacturing of rigid, semiflexible and flexible polyurethane foams, foamed elastomers and polyurethane molds.

The organic polyisocyanates are aromatic polyisocyanates (tolylene diisocyanates, diphenylmethane diisocyanates and the like), aliphatic polyisocyanates (hexamethylene diisocyanate and the like), alicyclic polyisocyanates (isophorone diisocyanate and the like), their modified products (for example, carbodiimide-modified), and their prepolymers having free isocyanate groups by their reactions with polyols.

The polyols are high molecular weight polyols, for example, the polyether-polyol having alkylene oxides (ethylene oxide, propylene oxide, 1,2- and 1,4-butylene oxide and the like) addition structure to water, polyhydric alcohols (glycols such as ethylene glycol, propylene glycol and the like; polyols having more than 3 OH-group such as glycerine, trimethylolpropane, triethanolamine, pentaerythritol, sorbitol, sugar and the like) and amine compounds (ethylene diamine, diethylene triamine, tolylene diamine, xylylene diamine, piperazine, N-aminoalkylpiperazine, N,N-dimethylaminopropylamine, cyclohexylene diamine and the like), polymerpolyols reacted the above polyetherpolyols with ethylenic unsaturated monomer (acrylonitrile, styrene, methyl methacrylate, butadiene, etc.) in the presence of polymerization catalyst such as the radical producer described in U.S. Pat. No. 3,383,351, polyester polyols reacted the above polyhydric alcohols with polycarboxylic acids (succinic acid, sebacic acid, maleic acid, adipic acid, fumaric acid, phthalic acid, dimeric acid and the like); polyesterpolyetherpolyols and mixtures of more than two kinds of the above-mentioned polyols.

In the present invention, crosslinking agents or chain extenders are also used with, if necessary, for example, low molecular weight polyols [triethanolamine, diethanolamine, ethylene glycol, diethylene glycol, butanediol, trimethylolpropane, glycerine, p-bis(2-hydroxyethyl) phenyleneether, etc.], and polyamines (tolylene diamine, xylylene diamine, diaminodiphenylmethane, methylene bis-o-chloroaniline and the like.

The blowing agents used in the present invention are halogen-substituted aliphatic hydrocarbons (Freon gas, methylene chloride and the like) and water.

And, if necessary, it is applicable to use with surfactants (silicone surfactants and the like), colors, fillers, flame-retardants and the like.

The used amount of the novel amidine compound and its salts with organic and inorganic acids in the present invention in generally 0.01 to 5 weight parts, perferably 0.1 to 2 weight parts for the 100 weight parts of polyol. In the case of less than 0.01 weight parts, the catalytic activity is too low and it takes a longer time to the completion of the reaction, and in the case of the use amount more than 5 weight parts, it is to decrease the physical properties, especially indentation load deflection (ILD).

The present invention will be illustrated further by using the following examples which do not provide any limitations on the scope (what is claimed) of the present invention.

EXAMPLE 1

Manufacturing method of DMA-DBU

3-Dimethylamino-2-oxohexamethylenimine (formula (2)) (468.6 g, 3.0 mole) was melted by heating at 70° to 90° C., and 9 ml of benzyl trimethyl ammonium hydroxide 30% methanol solution were added. Acrylonitrile (180.5 g, 3.3 mole) was added dropwise, requiring 50 minutes. The mixture was stirred further 3 hours at the same temperature. After unreacted acylonitrile was distilled off under reduced pressure, 328.6 g of the fraction boiling 141° to 145° C./0.5 mmHg were obtained. 1-Cyanoethyl-3-dimethylamino-2-oxohexamethylenimine (formula (4)), having 98.6% purity by gas-chromatography, was identified by specific infrared absorption of CN group (2250 $cm^{-1}$).

Into the mixture of the above cyanoethylated compound (305 g) and 11 g of Raney Nickel, 25 g of liquid ammonia was introduced under the pressure, and the cyanoethylated compound was hydrogenated at 100° to 120° C., under hydrogen pressure of 45 to 50 $kg/cm^2$ for about 3 hours. 298 g of crude 1-(3'-aminopropyl)-3-dimethylamino-2-oxohexamethylenimine (formula (3)) were obtained. The total amine value (HCl method) was 478.5, 91.0% of the theoretical value.

Then, to this 3-aminopropyl compound (285 g), 200 g of xylene and 2.9 g of p-toluenesulfonic acid were added, then stirred and heated for 150 hours. The water emerging from the intermolecular dehydration reaction was removed out of the reaction system as an azeotropic mixture. After the xylene was distilled off, the objective product (formula (1)) was purified by distillation under reduced pressure, yielding 125 g of oily product.

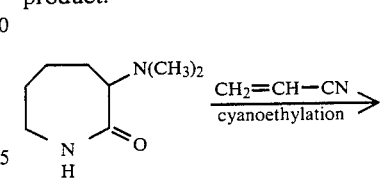

formula (2)

-continued

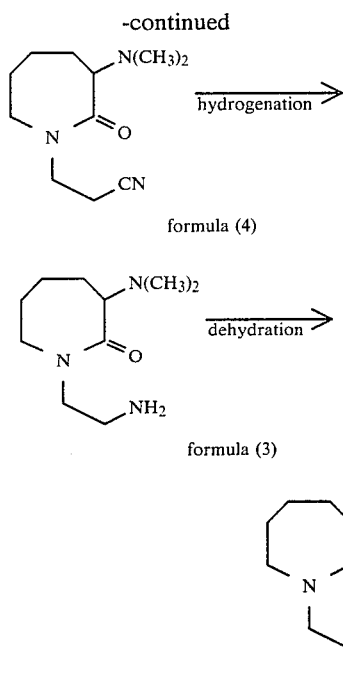

formula (4)

formula (3)

formula (1)

Boiling point 93.0° to 96.0° C./1 mmHg

Total Amine Value (HCl method): 288 [theoretical 287]

Total Amine Value (HClO₄ method): 573 [theoretical 574]

| $^1$H—NMR (DCCl$_3$, δ ppm) | $^{13}$C—NMR (δ ppm) |
|---|---|
| N(CH$_3$)$_2$ 6H S 2.15 | CH$_3$ 42.9 |
|  | C 6 on 7-membered ring 73.2 |

EXAMPLE 2

Comparison on water pick-up using DMA-DBU

On the bottom of a sealed container, saturated ammonium chloride solution (for 80% RH) and saturated sodium bromide solution (for 60% RH) was placed, respectively. About 5 g sample of DBU and DMA-DBU was weight exactly in a petri dish having a diameter of 6 cm, respectively. Then, the petri dishes were placed in the middle part of the sealed container. The sealed containers were kept at 25° C., and the weight increases by moisture absorption were determined over the period of 5 weeks.

$$\text{moisture absorption ration (\%)} = \frac{\text{weight increase}}{\text{sampling weight}} \times 100$$

The results were as shown in Table 1.

TABLE 1

| | \multicolumn{4}{c}{Trend of moisture absorption ratio with the passage of day} |
| | \multicolumn{4}{c}{relative humidity (% RH)} |
| | 80 | | 60 | |
| test sample | DMA/DBU | DBU | DMA/DBU | DBU |
|---|---|---|---|---|
| 1 (day after) | 15 | 25 | 10 | 18 |
| 2 | 19 | 34 | 11 | 23 |
| 3 | 21 | 41 | 11 | 26 |

TABLE 1-continued

| | \multicolumn{4}{c}{Trend of moisture absorption ratio with the passage of day} |
| | \multicolumn{4}{c}{relative humidity (% RH)} |
| | 80 | | 60 | |
| test sample | DMA/DBU | DBU | DMA/DBU | DBU |
|---|---|---|---|---|
| 6 | 25 | 57 | 11 | 32 |
| 10 | 30 | 70 | 12 | 38 |
| 13 | 35 | 75 | 12 | 42 |
| 21 | 39 | 78 | 13 | 48 |
| 28 | 40 | 79 | 13 | 51 |
| 35 | 42 | 80 | 13 | 53 |

As shown in Table 1, under the atmospheres both of 80% and 60%RH, the moisture absorption of DMA-DBU is low in comparison with that of DBU. The moisture absorption ratios of DMA-DBU are half to one quarter of those of DBU.

EXAMPLE 3

Change of pH of aqueous solution of DMA-DBU (hydrolysis)

One % aqueous solutions of DMA-DBU and DBU were prepared, respectively, and the changes of pH values with the passage of day were determined by using a glass electrode pH meter. The changes of pH were as shown in Table 2.

TABLE 2

| \multicolumn{3}{c}{Change of pH with the elapse of day} |
| kind of amidine | DMA-DBU | DBU |
|---|---|---|
| pH just prepared | 12.4 | 12.5 |
| 1 day after | 12.4 | 12.4 |
| 2 days after | 12.4 | 12.2 |
| 3 days after | 12.4 | 12.1 |
| 6 days after | 12.4 | 12.1 |
| 8 days after | 12.4 | 12.0 |
| 10 days after | 12.4 | 12.0 |

As shown in Table 2, the pH values of aqueous solution just prepared of DMA-DBU and DBU are nearly equal, and it is proved that DMA-DBU is a strong base equilavant to DBU. And moreover, as to these solutions, pH values of DMA-DBU become higher than those of DBU after 2 days from the preparation, and DBU is liable to be hydrolyzed in aqueous solution. On the other hand, DMA-DBU aqueous solution has no change in pH values, showing that DMA-DBU is not hydrolyzed.

EXAMPLE 4

Curing catalytic effect of DMA-DBU for epoxy resin-1, phenol novolac resin curing for cresol novolac epoxy resin Into one hundred parts (hereiafter parts by weight) of Sumi-epoxy ESCN 195XL (manufactured by Sumitomo Chemical Co., Ltd. cresol novolac epoxy resin, epoxy equilivent 199) and 55 parts of Barkham TD-2131 (manufactured by Dainippon Ink and Chemicals Incorp. phenol novolac resin, softening point 80° C.) 2 parts or 3 parts of DMA-DBU or DBU were added. The mixture was melted, mixed uniformly and pulverized. The power product was cured on a hot plate at the following temperatures, and the gel time was determined. The results were as shown in Table 3.

TABLE 3

Comparison of gel time on cresol novolac epoxy/phenol novolac (unit of gel time: second)

| kind of amidine | temperature | | | | | |
|---|---|---|---|---|---|---|
| | 160° C. | | 170° C. | | 180° C. | |
| | DMA/DBU | DBU | DMA/DBU | DBU | DMA/DBU | DBU |
| 3 | 45 | 51 | 30 | 36 | 21 | 26 |
| 2 | 60 | 66 | 40 | 46 | 27 | 32 |

As can be seen from Table 3, DMA-DBU showed shorter gel times than DBU at used amount levels both of 2 parts and 3 parts, and therefore DMA-DBU is regarded to have higher activity. O-Phthalic acid mono amidine salt containing 54% of DMA-DBU was prepared by heat-melting both raw ingredients. Six parts of each of the salts were added in the above formulation, and the gel times at 170° C. of the power product, obtained by the same treatment as the above, were determined. The DBU salt gave 38 seconds, while the DMA-DBU did 31 seconds, showing higher activity.

EXAMPLE 5

Curing catalytic effect of DMA-DBU for epoxy resin-2, liquid methyl hexahydrophthalic anhydride curing for liquid bisphenol A type epoxy resin To the mixture of 100 parts of liquid epoxy resin (diglycidyl ether of bisphenol A, Sumi-epoxy ELA-128, epoxy equivalent 186) and 90 parts of liquid acid anhydride (methyl hexahydrophthalic anhydride, HN-5500E manufactured by Hitachi Chemical Co., Ltd., acid value 667), 0.5, 1 or 2 parts of DMA-DBU or DBU were added and stirred to become uniform solution which was subjected to gel time deterioration at 100°, 120° or 150° C., according nearly to the test tube method of JIS C-2105.

TABLE 4

Comparison of gel time on liquid bisphenol A epoxy/methyl HHPA

| kind of amidine | temperature | | | | | |
|---|---|---|---|---|---|---|
| | 100° C. | | 120° C. | | 150° C. | |
| | DMA-DBU | DBU | DMA-DBU | DBU | DMA-DBU | DBU |
| 2 | 1,030 | 1,560 | 343 | 362 | 139 | 162 |
| 1 | 2,060 | 2,460 | 545 | 606 | 209 | 248 |
| 0.5 | 3,880 | 4,370 | 980 | 1,090 | 308 | 322 |

In comparison between DMA-DBU and DBU in gel times at respective temperatures and respective used amounts of amidines, the gel times of DMA-DBU are shorter than those of DBU, and DMA-DBU is comprehensively proved to have high activity.

In the case of the use of 1 part of 2-ethyl hexoic acid salt of (molar ratio 1:1) of DBU, the gel time at 120° C. was 1,010 seconds, and on the other hand in the case of 2-ethylhexoic acid salt (molar ration 1:1) of DMA-DBU, the gel time was 920 seconds under the same condition. Therefore DMA-DBU has higher activity than DBU in the case of their organic acid salts.

EXAMPLE 6

Pot life and curing on liquid epoxy resin/liquid acid anhydride system

To Example 5 formulation of liquid epoxy resin (100 parts) and liquid acid anhydride, 2-ethyl hexoic acid salt of DMA-DBU (1.2 parts) of Example 5 was added and stirred to be uniform solution. The viscossity was 210 cps at 40° C. The solution was kept at 40° C. and the pot life, the time required for the viscosity to attain to 1,000 cps (at 40° C.), was 24 hours.

Six grams of the above solution was placed in a die having 4 mm depth, and cured at 100° C. for 2 hours plus 130° C. for 6 hours. Then, colorless and transparent cured product was obtained.

EXAMPLE 7

Urethane catalytic effect of DMA-DBU

In ten grams of polyol having molecular weight 3,000 (glycerin propylene oxide adduct, Sannix G-P3000 manufactured by Sanyo Chemical Industries, Ltd., OH-value 56), 0.05 g of DMA-DBU or DBU was dissolved uniformly. To the mixture, 0.87 g of 80:20 mixture of 2,4-:2,6-isomer of tolylene diisocyanate was mixed, immediately sealed in a test tube, and kept at 70° C. The time required for the mixture to no longer flow was determined as the gel time.

The gel time of DBU is 7 minutes, while that of DMA-DBU was 5 minutes. From the comparison in gel time, it was found that DMA-DBU had higher activity than DBU.

EXAMPLE 8

Foaming example of urethane foam cured with DMA-DBU

To the polyol (100 parts) for Example 6, DMA-DBU (0.1 parts), water (4.5 parts), Silicone L-520 (2 parts) and stannous octoate (0.35 part) were added. To the above mixture, TDI-80 (54.8 parts) was added and stirred for 7 seconds by a high speed stirrer. The mixed content was placed in a carton box. The rise time was 80 seconds, obtaining good flexible urethane foam.

EXAMPLE 9

Manufacturing method of DBA-DBU

3-Dibutylamino-2-oxohexamethylenimine (formula(2)) (720 g, 3.0 mole) was melted by heating at 70° to 90° C., and 20 ml of Na-methoxide 30% methanol solution were added. Acrylonitrile (175 g, 3.3 mole) was added dropwise, requiring 50 minutes after the removal of methanol. The mixture was stirred further 3 hours at the same temperature. After unreacted acrylonitrile was distilled off under reduced pressure, 650 g of the fraction boiling at 175° to 185° C./1 mmHg was obtained. 1-Cyanoethyl-3-dibutylamino-2-oxohexamethylenimine (formula (4)), having 98.3% purity by gas chromatography, was identified by specific infrared absorption of CN group (2250 cm$^{-1}$).

Into the mixture of the above cyanoethylated compound (350 g) and 11 g of Raney Nickel, 25 g of liquid ammonia was introduced under the pressure, and the cyanoethylated compound was hydrogenated at 100° to 120° C. under hydrogen pressure of 45 to 50 kg/cm$^2$ for about 3 hours. 298 g of crude 1-(3′-aminopropyl)-3-dibutylamino -2-oxohexamethylenimine (formula (3)) was obtained. The total amine value (HCl method) was 370, 98.1% of the theoretical value.

Then, to this 3-aminopropyl compound (285 g), 200 g of pseudo cumene and 5.0 g of p-toluenesulfonic acid were added, then stirred at about 190° C. for 8 hours under nitrogen atmosphere. The water emerging from intermolecular dehydration reaction was

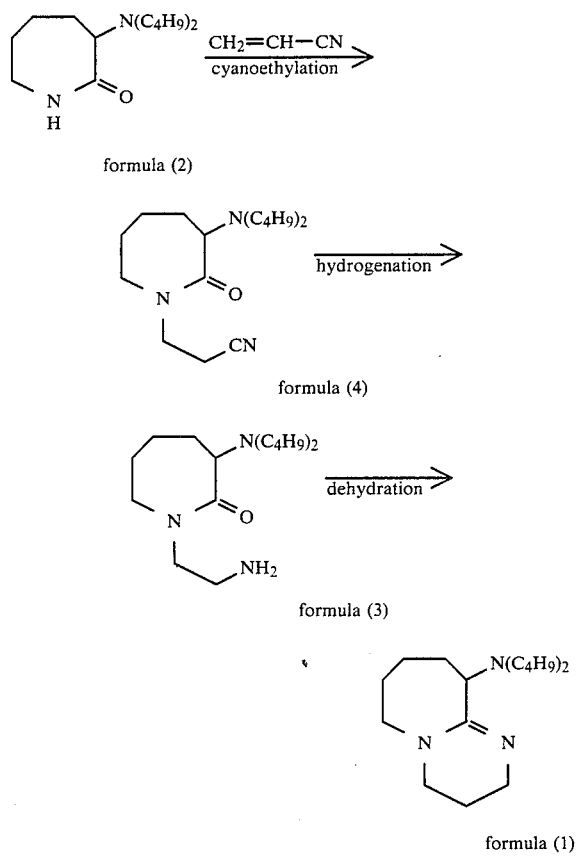

Boiling point 148° to 157° C./1 mmHg
Total Amine Value (HCl method): 201 [theoretical 201]
Total Amine Value (HClO$_4$ method): 400 [theoretical 402]
Tertiary Amine Value (HCl method): 201 [theoretical 201]

EXAMPLES 10 AND 11

Manufacturing method of MOA-DBU and BB$_z$A-DBU

3-Methyloctylamino-1,8-diazabicyclo (5,4,0) undecene-7 (MOA-BDU) and 3-butylbenzylamino-1,8,diazobicyclo (5,4, ))undecane-7 (BBzA-DBU) were obtained in a similar manner to Example 9. Their physical properties and analytical data are shown in Table 6.

TABLE 6

Physical properties of MOA-DBU and BBzA-DBU

| Example (Compound) | Example 2 (MOA-DBU) | Example 3 (BBzA-DBU) |
|---|---|---|
| Appearance | Slight yellow oil | Yellow oil |
| Boiling point (1 mmHg) | 155 to 166° C. | 176 to 188° C. |
| Total Amino Value (HCl method) | 192(theoretical 191) | 181(theoretical 179) |
| Total Amino Value (HClO$_4$ method) | 379(theoretical 383) | 351(theoretical 358) |
| Tertiary Amine Value (HCl method) | 189(theoretical 191) | 176(theoretical 179) |
| Purity by gaschromatography | 98.6% | 97.9% |
| Solubility to water | Insoluble | Insoluble |

EXAMPLE 12

Curing catalytic effect for epocy resin phenol novolac resin curing for cresol novolac epoxy resin Into one hundred parts (hereafter parts by weight) of Sumi-epoxy ESCN 195XL (manufactured by Sumitomo Chemical Co., Ltd, cresol novolac epoxy resin, epoxy equilivant 199) and 55 parts of Barkam TD-2131 (manufactured by Dainippon Ink and Chemicals Incorp., phenol novolac resin, softening point 80° C.) 2 parts of DBA-DBU or DBU were added. The mixture was melted, mixed uniformly and pulverized. The powder product was cured on a hot plate (170° C.), and the gel time was determined. The gel time of DBU was 46 second, and that of DBA-DBU was 46 seconds and that of DBA-DBU was 47 seconds, showing equivalent catalytic activity.

EXAMPLE 13

Water absorption ratio of epoxy resin

To the mixture of 100 parts of liquid epoxy resin (diglyeidyl ether of bisphenol A, Sumi-epoxy ELA-128, epoxy equivalent 186) and 90 parts of liquid acid anhydride (methyl hexahydrophthalic anhydride, HN-5500E manufactured by Hitachi Chemical Co., Ltd., acid value 667), 1 or 2 parts amidine compounds were added and stirred to become uniform solution. Six grams of this solution was placed in a die having 4 mm thickness, and cured at 100° C. for 2 hours plus at 130° C. for 7 hours. The cured product was colled to room temperature in a desicater. The water absorption ratios of thus obtained test specimens were determined under the conditions shown in Table 7.

| Kind of Amidine | DBA-DBU | | DBU | |
|---|---|---|---|---|
| pbw of amidine | 1 pbw | 2 pbw | 1 pbw | 2 pbw |
| Tg (TMA) of cured specimen | 130° C. | 132° C. | 130° C. | 131° C. |
| Water absorption ratio of cured product (%) | | | | |
| (1) dripping in water at 23° C. for 24 hours | 0.18 | 0.18 | 0.19 | 0.21 |
| (2) dripping in boiling water for 1 hour | 0.29 | 0.29 | 0.31 | 0.33 |

As shown in Table 7, the water absorption ratios of test specimens cured with DBA-DBU were lower than those with DBU, and moreover the ratios were not changed with the used amount of DBA-DBU.

EXAMPLE 14

Foaming example of urethane foam having polyvinylchloride (PVC) sheet and discoloration of PVC sheet So-called cold-cure-foams having PVC sheet were prepared by using the under-cited foaming formulation. The foams were placed in an oven at 120° C. and the discolorations of PVC sheet were observed.

Temperature of raw ingredients: 25° C.

Temperature of cast iron mold (20×20×1 cm): 40° C.

Mold release agent: Bond Wax URT-35T (Made by Bond Wax K.K)

Cure condition: 10 minutes at room temperature

Foaming formulation*

|  | (pbw) |
| --- | --- |
| SANNIX FA-703 | 100 |
| Triethanolamine | 4 |
| Water | 2.5 |
| Catalyst | 1.0 |
| Crude MDI (105 index) | 58.9 |

*SANNIX-FA-703 (manufactured by Sanyo Chemical Industries, Ltd.) An ethylene oxide-chipped polyol composition having analytical values of color (APHA) less than 75, OH-value 33±5, pH 5.5 to 7.5, moisture less than 0.1% and viscosity 800±50 cps. at 25° C.

A light brown sluch molding PVC sheet was set in advance inside of mold by using both-sides adhesion tape.

Into the uniform mixture consisting of raw ingredients, except crude MDI, shown in the above foaming formulation, a calculated amount of crude MDI was added, stirred for 7 seconds by high speed stirrer, and then poured into the above mold.

When DBA-DBU was used as the catalyst, a good mold foam having PVC sheet and total density (except PVC sheet, 0.14 g/cm², hereafter total density is the same representation). When MOA-DBU and BBzA-DBU were used as the catalyst, good mold foams similar to DBA-DBU foams were obtained. The total densities were 0.13, 0.14, respectively. When DBU was used as the comparative catalyst example, the total density was 0.14.

Thus obtained mold foams having PVC sheet were placed in an oven at 120° C. and the discoloration of PVC sheet was observed.

TABLE 8

| Name of Catalyst | Discoloration of PVC sheet | |
| --- | --- | --- |
|  | after 24 hrs. | after 72 hrs. |
| DBA-DBU | no change | no change |
| MOA-DBU | " | " |
| BBzA-DBU | " | " |
| DBU (comparative) | The edge part only was black-brown colored. | All surface was black-brown colored. |

The novel amidines obtained in the present invention have lower water solubilities and are less hygroscopic in comparison with DBU. And moreover, the novel amidines in the present invention have comparable activities as the epoxy catalyst to DBU activity. When they are used as the urethane catalyst, the discoloration of PVC of the mold foam having PVC sheet is remarkably improved in comparison with that of DBU foam. They are useful as the catalyst for epoxy composition and for manufacturing various kinds of polyurethane.

What is claimed is:

1. An amidine compound represented by the following formula

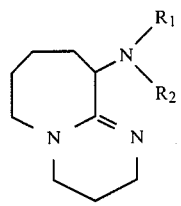

wherein each $R_1$ and $R_2$ is independently an alkyl group having $C_1$ to $C_{14}$ or benzyl group and the sum of carbon atoms is 2 to 16.

2. The amidine compound of claim 1, wherein $R_1$ and $R_2$ are $-CH_3$.

3. The manufacturing method of an amidine compound having the formula

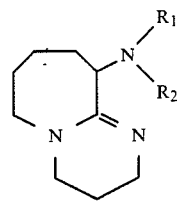

which comprises cyanoethylation of the lactam compound represented by the following formula (2), the reduction and finally, cyclization by dehydration:

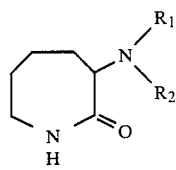

formula (2)

wherein each of $R_1$ and $R_2$ is independently an alkyl group having $C_1$ to $C_{14}$ or benzyl group and the sum of carbon atoms is 2 to 16.

4. The manufacturing method of claim 3, wherein $R_1$ and $R_2$ are $-CH_3$.

5. The application method of curing epoxy resins which comprises curing said epoxy resins in the presence of an amidine compound having the following formula, or its salts:

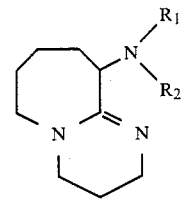

wherein each of $R_1$ and $R_2$ is independently an alkyl group having $C_1$ to $C_{14}$ or benzyl group and the sum of carbon atoms is 2 to 16.

6. The method of claim 5, wherein $R_1$ and $R_2$ are $-CH_3$.

7. The application method of hardening isocyanate resin which comprises hardening said isocyanate resin in the presence of an amidine compound having the following formula or its salts:
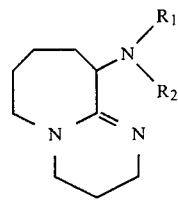
wherein each of $R_1$ and $R_2$ is independently an alkyl group having $C_1$ to $C_{14}$ or a benzyl group and the sum of carbon atoms is 2 to 16.
8. The application method of claim 7, wherein $R_1$ and $R_2$ are —$CH_3$.
* * * * *

UNITED STATES PATENT AND TRADEMARK OFFICE
CERTIFICATE OF CORRECTION

PATENT NO. : 4,683,249

DATED : July 28, 1987

INVENTOR(S) : Keiichi Nakatani et al.

It is certified that error appears in the above-identified patent and that said Letters Patent is hereby corrected as shown below:

Column 7, lines 10 to 25 :

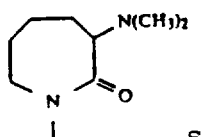  should be  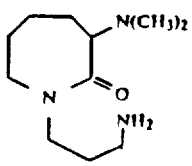

formula (3)

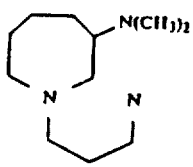  should be  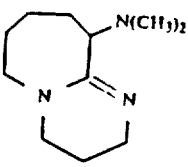

formula (1)

UNITED STATES PATENT AND TRADEMARK OFFICE
CERTIFICATE OF CORRECTION

PATENT NO.   :   4,683,249

DATED        :   July 28, 1987

INVENTOR(S)  :   Keiichi Nakatani et al.

It is certified that error appears in the above-identified patent and that said Letters Patent is hereby corrected as shown below:

Column 9 line 34:   change "deterioration" to --determination--

Column 11, lines 35 to 40:

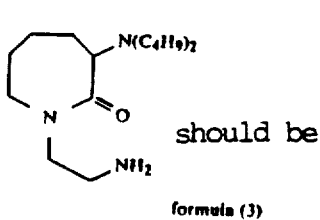

formula (3)

should be

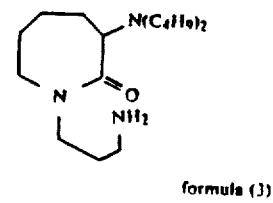

formula (3)

Signed and Sealed this

Second Day of February, 1988

Attest:

DONALD J. QUIGG

Attesting Officer

Commissioner of Patents and Trademarks